(12) United States Patent
Kindlein et al.

(10) Patent No.: US 7,217,235 B2
(45) Date of Patent: May 15, 2007

(54) SOLID STATE BRACHYTHERAPY APPLICATOR

(75) Inventors: Johann Kindlein, Toenisvorst (DE); Rudolf Leonard Josef Scholte, Amersfoort (NL)

(73) Assignee: Nucletron B.V., Veenedaal (NL)

( * ) Notice: Subject to any disclaimer, the term of this patent is extended or adjusted under 35 U.S.C. 154(b) by 305 days.

(21) Appl. No.: 10/811,938

(22) Filed: Mar. 30, 2004

(65) Prior Publication Data

US 2005/0074093 A1   Apr. 7, 2005

(30) Foreign Application Priority Data

Oct. 3, 2003   (EP) ................... 03078121

(51) Int. Cl.
*A61N 5/00*   (2006.01)

(52) U.S. Cl. ............................. 600/1; 378/65
(58) Field of Classification Search ................ 600/1–8; 378/64–65, 121–138, 119
See application file for complete search history.

(56) References Cited

U.S. PATENT DOCUMENTS

| 5,729,583 A | 3/1998 | Tang et al. |
| 6,320,935 B1 | 11/2001 | Shinar et al. |
| 6,477,233 B1 | 11/2002 | Ribbing et al. |

FOREIGN PATENT DOCUMENTS

| DE | 198 29 444 A | 1/2000 |
| DE | 198 54 287 A1 | 6/2000 |
| EP | 0 860 180 A2 | 8/1998 |
| EP | 1 316 330 A1 | 6/2003 |
| WO | WO 97/07740 A1 | 3/1997 |
| WO | WO 01/85255 A1 | 11/2001 |

*Primary Examiner*—John P. Lacyk
(74) *Attorney, Agent, or Firm*—Birch, Stewart, Kolasch & Birch, LLP

(57) ABSTRACT

The invention relates to a solid state brachytherapy applicator for performing radiation therapy treatment in an animal body, said applicator at least comprising an X-ray emitting surface composed of: a vacuum cavity containing a cathode and an anode spaced apart at some distance from each other; emitting means for emitting free electrons from the cathode; electric field means for applying during use a high-voltage electric field between said cathode and said anode for accelerating said emitted free electrons towards said anode; wherein said vacuum cavity being at least partly transparent to X-ray radiation emitted by said anode.

Figure 5:
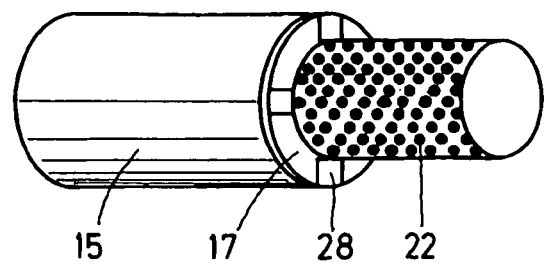

The invention furthermore relates to a radiation therapy treatment system for performing radiation therapy treatment in an animal body and to a method for performing radiation therapy treatment in an animal body using a solid state brachytherapy applicator according to the invention.

According to the invention said vacuum cavity is bound by first and second plate-shaped elements spaced some distance from each other, said first plate-shaped element serving as cathode and said second plate-shaped element serving as anode.

15 Claims, 3 Drawing Sheets

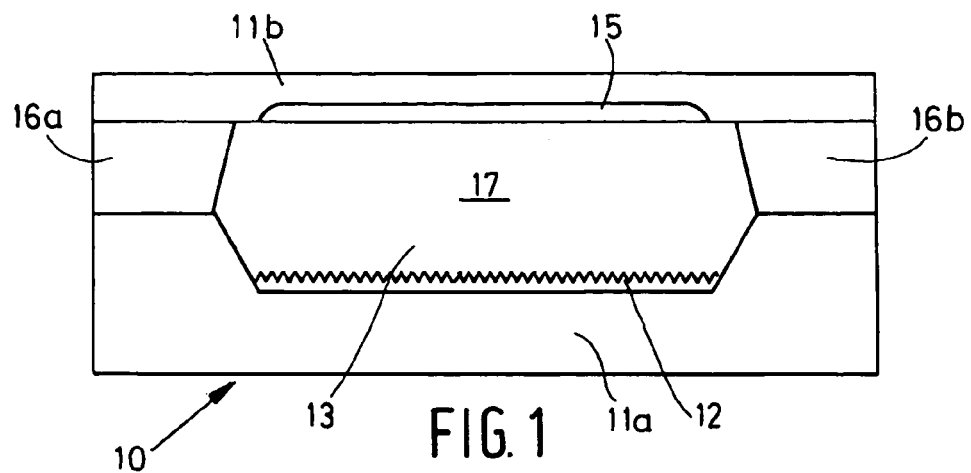
FIG. 1
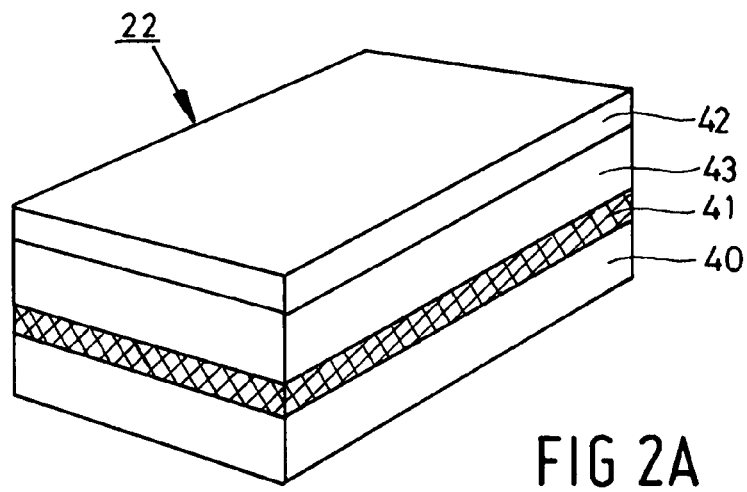
FIG 2A
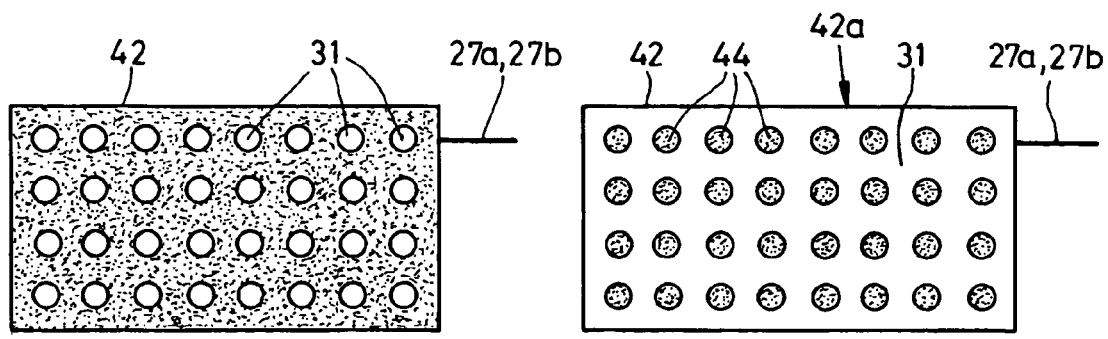
FIG. 2B
FIG. 2C

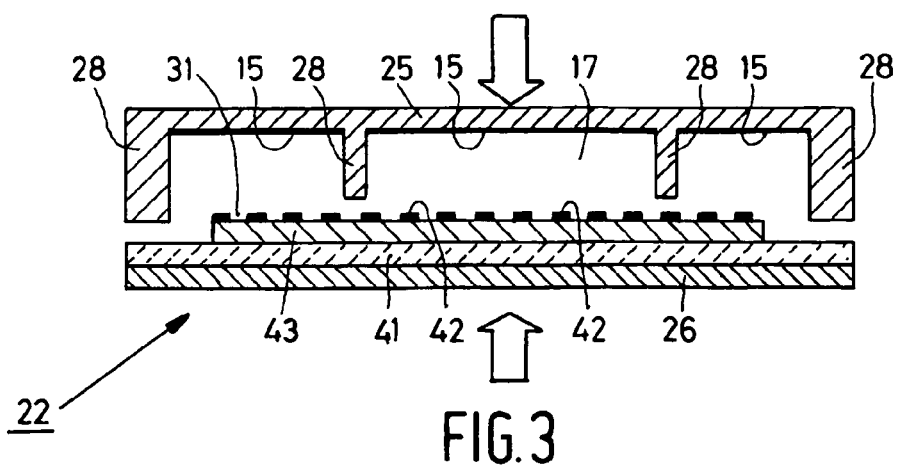
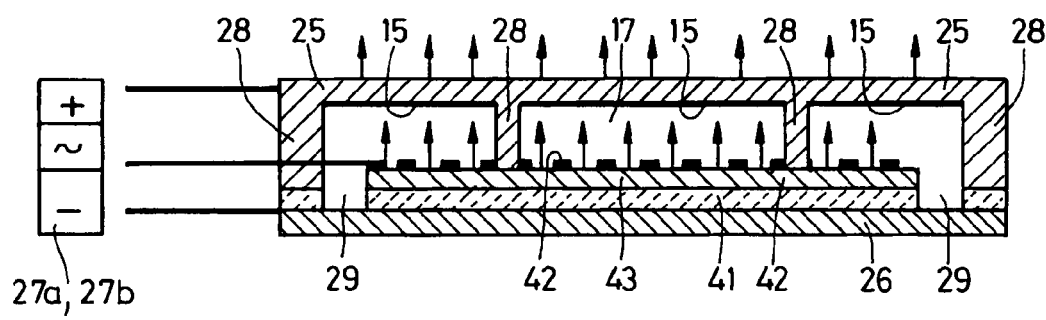
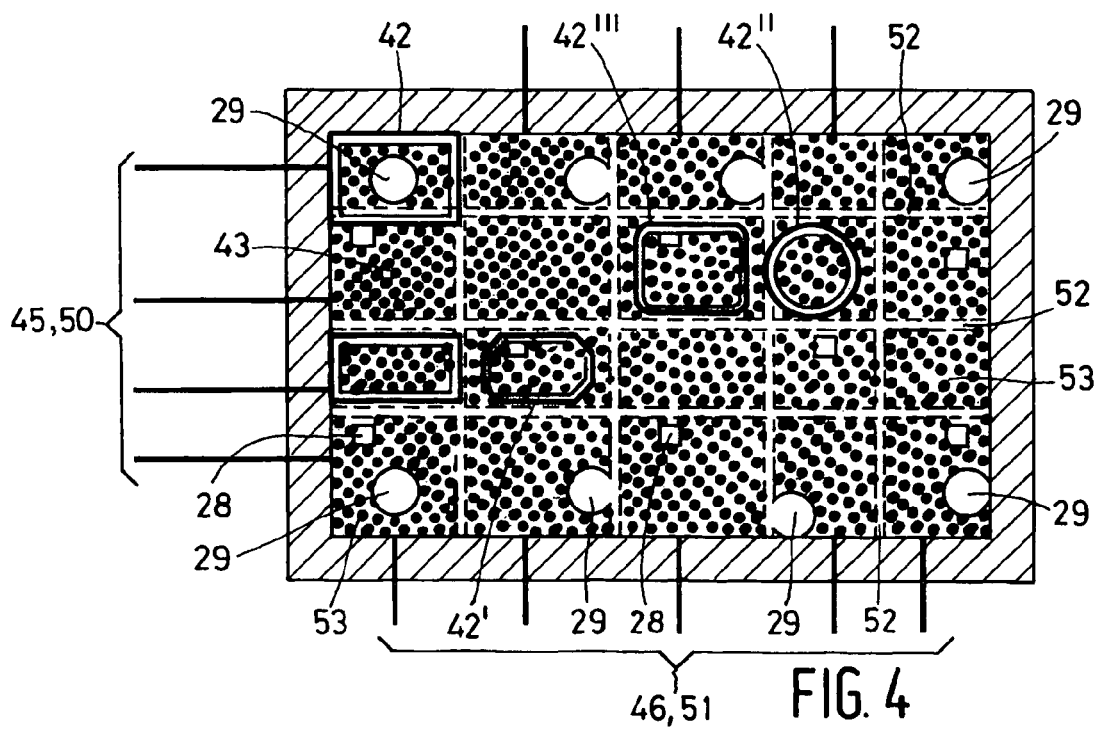

SOLID STATE BRACHYTHERAPY APPLICATOR

This Nonprovisional application claims priority under 35 U.S.C. § 119(a) on Patent Application No. 03078121.5 filed in EUROPE on Oct. 2, 2003, the entire contents of which are hereby incorporated by reference.

DESCRIPTION

The invention relates to a solid state brachytherapy applicator for performing radiation therapy treatment in an animal body, said applicator at least comprising an X-ray emitting surface composed of:

a vacuum cavity containing a cathode and an anode spaced apart at some distance from each other;

emitting means for emitting free electrons from the cathode;

electric field means for applying during use a high-voltage electric field between said cathode and said anode for accelerating said emitted free electrons towards said anode; wherein said vacuum cavity being at least partly transparent to X-ray radiation emitted by said anode.

The present invention relates to a generation of X-rays for medical purposes.

The invention furthermore relates to a radiation therapy treatment system for performing radiation therapy treatment in an animal body using a solid state brachytherapy applicator according to according to the invention.

Radiation therapy is a well-established method for treatment of several diseases, including cancer. The presumptive usefulness of an X-ray source device is clear. The insertion of the device into vessels or other body cavities would allow the delivered radiation dose to be confide to a small tissue region.

An X-ray source device according to the above preamble is for example known from U.S. Pat. No. 6,477,233 B1. In this patent publication an embodiment of an X-ray source device is disclosed, having a vacuum cavity, wherein a cathode and an anode spaced apart are accommodated.

The vacuum cavity is to be evacuated to a preferred vacuum level required for a proper operation of the X-ray source device. Furthermore, the known X-ray source device is provided with electric field means for establishing a high-voltage electric field between the anode and cathode. Electrons emitted from said cathode are accelerated by said established high-voltage electric field and impact with a high kinetic energy on said anode material. In the anode material X-ray radiation is generated with a high energy level.

As the vacuum cavity is entirely highly transparent to X-ray radiation, said generated radiation can leave the vacuum cavity towards the patient's tissue in which the X-ray source device is inserted. As the generated X-ray radiation leaving the X-ray source device exhibits a high energy level, the X-ray radiation is highly suitable for performing radiation therapy in said patient's body, for example for treating cancer tumours.

Although the known X-ray source device is highly suitable for treating cancer tumours in a patient's body it is primarily intended to be introduced in said patient's body through a catheter tube. Furthermore due to its small dimensions the source device can be regarded as a point-like source of X-ray radiation with a spherical doses distribution.

According to the invention said vacuum cavity is bound by first and second plate-shaped elements spaced some distance from each other, said first plate-shaped element serving as cathode and said second plate-shaped element serving as anode. Due to its enlarged surface area the plate-shaped vacuum device can be brought into direct contact with the tissue or organ of the patient of a significant area or size, thus establishing an enlarged doses distribution towards said locations within the patient's body.

It should be note that the X-ray source device according to the invention exhibit longitudinal dimensions (length and width) substantially greater than the thickness (being the space between the anode and cathode) of the device.

In order to maintain an equal distance between the anode and cathode even over a significant large surface area spacers of high insulating material are present between said first and second plate-shaped elements.

In order to assure an efficient acceleration of the free electrons emitted from said cathode towards the anode a significantly low vacuum level within the vacuum cavity is required. A significant low vacuum level is also necessary to prevent a gas discharge of the gas molecules still present in said vacuum cavity or to avoid the forming of an electrical arc within said vacuum cavity. Further a total destruction of the assembly is also possible.

To this end in a specific embodiment a getter material is provided on the surface of said first plate-shaped element facing away from said second plate-shaped element. The getter material will react and bond with any stray gas molecule still present within the vacuum cavity. The getter, therefore, eliminates stray gas molecules, thereby improving the quality of the vacuum level within the vacuum cavity up to $10^{-7}$ to $10^{-8}$ Torr.

More in particular said first plate-shaped element is provided with at least one opening exposing said getter material to said vacuum cavity. More in particular said first plate-shaped element is made from segments. The getter material is therefore mounted at a location between the segments, where no electric field between the anode and cathode exits. An essentially electric field free location of electrically isolated the getter material is required as therefore the getter would not present any internal electrical problems associated with surface arcing or breakdown. With this construction stray gas molecules can still be captured improving the vacuum level within the vacuum cavity.

Advantageous embodiment of said X-ray source device according to the invention are characterized in that said vacuum cavity is shaped having a complex, spatial geometry, which can be spheres, semi-spheres, cylinders or plates.

In a further advantageous the X-ray source device is connected to a distal end of a guiding wire for insertion towards said desired location within an animal body.

In a specific embodiment of the invention said first plate-shaped element serving as cathode is of a gated field emission type, like a ferro-electric electron emitting ceranic (PZT, PLZT) material or nano-tubes.

In case of using a ferro-electric electron emitting cathode the ferro-electric electron emitting material is positioned between a lower electrode and an upper electrode, both electrodes being connected to a driving voltage.

In a more advantageous embodiment said lower electrode (the cathode) is build up from several electrode segments, the segments of said electrode being electrically isolated from each other and each separately being connected to said driving voltage. As the driving voltage of each segment can be separately activated and switched off with this embodiment of the cathode the electron flux towards the anode can be controlled in a sophisticated manner and a more versatile radiation dose distribution emitted by the anode can be generated tailored specifically to certain radiation therapy treatments.

A more versatile use of the X-ray source device having these features is obtained as in a specific embodiment said electrode segments of said lower electrode are each separately connected to said driving voltage via a multiplexer.

Via said multiplexer a sophisticated electronic control of the X-ray source device is obtained capable in producing X-ray radiation with specific dose distribution intended for performing a specific radiation treatment.

The upper electrode is constructed as an electrically conductive sheet provided with a large number of small circular openings or stripes serving as emitting surfaces for the emitted free electrons, wherein said openings have a polygonal shape, for example round, square, hexagonal, etc. In general the cathode elements could have different shapes and have an important influence on the shape of the dose distribution of the radiation being emitted by the anode.

In another embodiment said upper electrode is constructed as at least one electrically conductive frame in which a large number disc shaped elements is fixed on the ferro-electric electron emitting material. In case when the cathode is made of carbon nanotubes the carbon nanotubes are fixed on the segment surfaces of the cathode.

The invention also relates to radiation therapy treatment system for performing radiation therapy treatment in an animal body at least comprising a doses planning device for preplanning a radiation therapy treatment within said animal body using an X-ray source device according to the invention, control means for driving said X-ray source device according to the preplanned therapy treatment and one or more radiation detectors positioned in the near vicinity of said source device in said animal body for measuring the actual radiation dose distribution generated by said X-ray source device, and wherein said radiation therapy treatment system is arranged for delivering feedback information to the control means to adapt the dose according to the preplanned treatment parameters.

Figure 6:
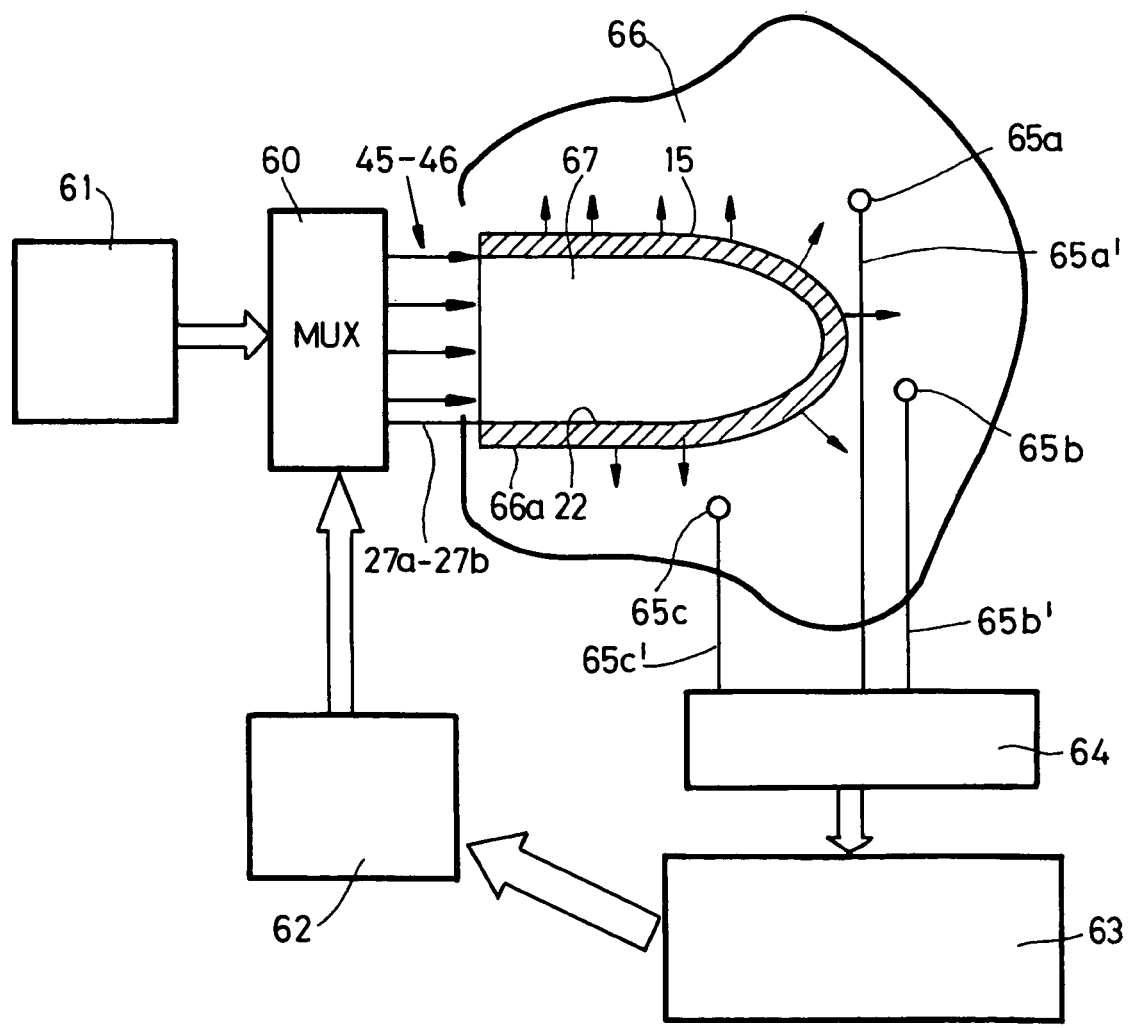

The invention will now be described with reference to a drawing which drawing shows:

FIG. 1 discloses an X-ray source device according to the state of the art;

FIG. 2A–2C disclose further detailed views of a specific feature of an X-ray source device according to the invention;

FIGS. 3–5 disclose further embodiments of an X-ray source device according to the invention;

FIG. 6 discloses a radiation therapy treatment system for performing radiation therapy treatment using an X-ray source device according to the invention.

In FIG. 1 a known X-ray source device according to the state of the art is disclosed showing the X-ray source device in a longitudinal cross-section. The X-ray source device 10 according to the prior art comprises a base 11a and a cover 11b interconnected via insulating members 16a–16b. The base element 11a can be made of Si or other semiconductor material, glass, ceramic materials or metal, and has a depression 13 formed therein.

A cavity 17 is formed between said base element 11a and said cover element 11b. The cover can be made of e.g. Si or other semiconductor material, glass, ceramic materials or metal, or of a combination of metal/semiconductor. The cavity 17 is evacuated.

Within the depression 13 a thin film cathode 12 is placed, whilst the inner surface of the cover 11b is provided with anode material 15. The cathode material 12 consist of an electron emitting material from which electrons are freed using techniques already known in the art.

Although not shown in FIG. 1 in general a known X-ray source device according to the state of the art is further provided with means for establishing a high-voltage electric field between the anode 15 and cathode 12. To this end the anode material 15 is connected with an supply wire connected with a high-voltage source (not shown).

The electrons freed from said cathode material 12 are accelerated by said high-voltage electric field and impact on the anode material 15. Due to the high velocity of the electrons specific X-ray radiation is generated within the anode material. The X-ray radiation will escape the vacuum cavity 17 towards the tissue of the patient in which The X-ray source device is implanted due to the fact that the cover 11b is manufactured from a material which is highly transparent for X-ray radiation.

In a preferred embodiment of the X-ray source device according to the invention the cathode is of a gated field emission type with a ferro-electric emitter allowing to control the electron flow more accurately independent of the accelerating high-voltage applied for generating the high-voltage electric field between the anode and the cathode.

In FIG. 2a said ferro-electric electron emitting material 43 is positioned between a lower electrode 41 and an upper electrode 42, both electrodes being connected to said emitting means. The whole assembly can be supported by a support or substrate 40.

By applying a controlled voltage difference between the lower and upper electrodes 41, 42 of the cathode 22 the electron current from the ferro-electric material 43 towards the anode 25 can be modulated or even cut-off entirely. The driving voltage applied to the ceramic cathode depends on the state of the ferro-electric material, that is the crystal phase and the thickness thereof. The driving voltage for freeing electrons from the ferro-electric material decreases as the thickness of the cathode layer decreases. Furthermore the magnitude of the driving voltage is largely dependent on the size of the electron emitting region, that is the electron emitting whole size on the driving electrodes.

In order to further control and improve the free emission of electrons from the ferro-electric material 43 said upper electrode 42 is constructed as an electrically conductive sheet provided with a large number of openings 31. These openings 31 serve as emitting holes for the emitted free electrons. In FIG. 2b said specific embodiment of this feature is disclosed.

Another embodiment of this feature is shown in FIG. 2c, wherein said upper electrode 42 is constructed as an electrically conductive frame 42a in which a large number disc shaped elements 44 are fixed on said ferro-electric electron emitting material 43 (31). The exposed ferro-electric material 43 (indicated in FIG. 2c with reference numeral 31) is capable of emitting electrons.

In FIG. 3 a first embodiment of an X-ray source device according to the invention is disclosed. According to the invention said vacuum cavity 17 is bound by first and second plate-shaped elements 22-15, 25 spaced some distance from each other, wherein said first plate-shaped element 22 serves as cathode and said second plate-shaped element 15, 25 serves as anode. Reference numeral 25 denotes said second plate-shaped element, wherein reference numeral 15 depict a layer of anode material deposited on said second plate-shaped element.

The X-ray source device according to the invention hence exhibit a plate-shaped configuration with substantial larger dimensions in length and width as in thickness.

An embodiment is for example shown in FIG. 5, where the X-ray source device is shaped as a cylinder having small outer dimensions, but an enlarged radiation emitting surface. This embodiment is highly suitable to be connected to the distal end of a wire for insertion through a catheter. However also other spatial geometries are possible like a semi-spherical or plate-shaped X-ray source device.

When shaped as a semi-spherically plate-shaped X-ray source device the anode 15 can be positioned on the outer or inner surface of the spatial geometry. In the first embodiment the X-ray source device is suitable for placement into a body cavity of a patient, thereby equally treating the tissue of said body cavity surrounding the X-ray source device with X-ray radiation having a dose distribution conformal to the spatial geometry of the X-ray source device.

Returning to FIG. 3 the first and second plate-shaped elements 22 and 25 are spaced apart from each using several spacers 28. Thus even over larger surface area's a vacuum cavity 17 is obtained with an overall equal thickness. As both the anode and cathode are connected to a high-voltage supply for establishing a high-electric field between the anode and cathode for the purposes of accelerating the free electrons emitted by the cathode.

A first method for manufacturing a cathode 22 as disclosed in FIGS. 2 and 3 is based on the use of a gold paste, which is formed on the substrate 40 (FIG. 2) using a printing method. This gold layer is then plasticized with a thin layer (reference numeral 39 in FIG. 3) for a predetermined time to form the lower electrode layer 41.

When the lower electrode layer 41 is completed a paste of PZT or PLZT is applied to a thickness of some tenths of micrometers using a printing method and then plasticized to form the ferro-electric electron emitting layer 43. Finally the upper electrode 42 is formed having a plurality of fine emission holes 31 using a printing method. The upper electrode 43 is also plasticized again and the desired cathode body 22 is obtained as shown in FIGS. 2a, 2b and 3.

Also another method than the printing method can be employed, for example sputtering.

Yet an another manufacturing method consists in gold evaporation of the upper electrode 42 on the ferro-electric electron emitting layer 43 with a mask of 50 μm in diameter islands 44 with a inter-distance of 50 μm, thus obtaining the embodiment of FIG. 2c.

As material for the plate-shaped anode support 25 alumina, beryllium, or pyrolytic boron-nitride could be used. The anode material 15 can be formed by a variety of techniques, preferably by electro-deposition. Other techniques, however such as laser deposition, chemical vapour deposition and physical vapour deposition may be used and are known in the art. After forming the anode material 15 on support 25 the anode housing assembly is cleaned and heat treated.

Typically, the assembly 15–25 is washed in distilled water. The assembly may be heat treated in a vacuum of $10^{-5}$ $10^{-7}$ millibars. The heat treatment within the vacuum furnace may be carried out at a temperature of 800° C. for 15–30 minutes. Heat treating increases adhesion of the anode material 15 to the anode assembly 25 and removes residual hydrogen, among other gases from the housing to increase its resistivity.

Considering the severe demand on permeability a dense sintered low-porosity alumina is one of the best choices for the support 25 of the anode material 15. Alumina is also compatible from the thermal expansion with tungsten used as a common material in x-ray tubes.

The anode assembly 15–25 and the cathode assembly 22 are fixed together by appropriate brazing alloys (Ticusil, Incusil, 15 ABA and Incusil-ABA), which comprises indium, titanium, copper and silver at different percentages. All components including spacers 28 are baked at 500° C. for 1 hour and subsequently they are pressed together (see the two arrows in FIG. 2) and the temperature has to be ramped up to 830° C. for fixation. The vacuum 17 inside of the structure is performed thereafter by connecting the X-ray assembly with a vacuum pomp.

A specific embodiment of the X-ray source device according to the invention is shown in FIG. 4. Identical parts are denoted with the same reference numeral.

On the surface of said first plate-shaped element 22 facing away from said second plate-shaped element 25, hence on the first lower electrode 41 a getter material 26 is provided. More in particular said first lower electrode 41 is provided with at least one opening 29 exposing said getter material 26 to said vacuum cavity 17. These features have several advantages.

With the positioning of the getter material between the cathode segments facing away from the anode said getter material is not mounted in the electrical field established between the anode 25 and cathode 22. Instead it is mounted at a location where no electric field exits. An essentially electric field free location of the getter material is required as therefore the getter material 26 would not present any internal electrical problems associated with surface arcing or breakdown.

The presence at least one opening thereby exposing said getter material 26 to said vacuum cavity 17 allows the getter material to react and bond with any stray gas molecule still present within the vacuum cavity 17. The getter material 26, therefore, eliminates stray gas molecules, thereby improving the quality of the vacuum level within the vacuum cavity 17 up to $10^{-7}$ to $10^{-8}$ Torr.

Moreover other specific features of a plate-shaped X-ray source device according to the invention is disclosed in FIG. 4. In FIG. 4 the lower 41 and upper 42 electrodes are build up from several electrode segments 53 in this embodiment dividing each plate-shaped electrode 41–42 in a matrix of orthogonal rows 50 and columns 51. The segments 53 each electrode 41–42 are electrically isolated from each other by means of isolation stripes or barriers 52. Further more each row 50 and column 51 of segments 53 are separately connected via connections 45, 46 to a driving voltage 27a–27b via a multiplexer MUX 60 (see FIG. 6).

With the multiplexer 60 it is possible to apply in a specific controllable manner a voltage difference between corresponding segments 53 via one of the row connections 45 and one of the column connections 46. This allows to activate specific parts the cathode 22 thereby generating a specific free electron flux impinging on the anode 25. With this configuration specific radiation distributions can be generated depending on the radiation therapy to be performed.

By applying a controlled voltage via the matrix shaped layout of connections 45, 46 to the segments 53 of the lower and upper electrodes 41–42 the electron current (free electron flux) emitted form the activated the cathode segments 53 towards the anode 15 can be limited or modulated and even cut off entirely.

The driving voltage applied to the cathode-assembly 22 depends on the state of the ferro-electric material used, i.e. the crystal phase and thickness thereof. The driving voltage decrease as the thickness of the ferro-electric layer 43 decreases. Moreover, the magnitude of the driving voltage largely depends on the size of the electron emission region or segment, i.e. the size of the electron emission holes 31 or islands 44 as shown in FIGS. 2*b* and 2*c*.

In FIG. 6 another implementation of the invention is disclosed. FIG. 6 depicts a radiation therapy treatment system for performing radiation therapy treatment in an animal body 66 using an embodiment of an X-ray source device 67 as depicted and described in this application.

In this embodiment the plate-shaped X-ray source device according to the invention exhibits a complex, spatial geometry and is placed within a body cavity 66*a* of a patient 66. Said body cavity can for example be a cavity created after surgery for temporarily performing radiation therapy treatment during surgery.

The anode 15 is positioned on the outer surface of the plate-shaped X-ray device 67. In this treatment application the tissue of body cavity 66*a* surrounding the X-ray source device 67 is exposed to the X-ray radiation emitted by the anode 15.

The cathode 22 is of a gated field emission type containing a ferro-electric electron emitting material as described in FIGS. 2–4 and is connected to a high-voltage supply 61 via multiplexer MUX 60 aand via electric connections 27*a*–27*b*, 45–46. As described in conjunction with FIG. 4 MUX 60 applies a voltage difference between corresponding segments of first, lower electrode 41 and second upper electrode 42 thus generating a free electron flux towards the anode 15 having a specific configuration.

The free electrons impinge on the anode 15 generating X-ray radiation directed to the tissue of the body cavity 66*a* surrounding the device 66.

MUX 60 (and thus the ferro-electric cathode) is controlled by control means 62, which control means 62 in turn are driven by a treatment planning system 63. In treatment planning system 63 a preplanned radiation treatment for said patient 66 is stored, containing information relating to the patient's internal organs, where the treatment is to be performed (image information), as well as dose distributions, dwell times (exposure times), etc. etc.

Several radiation sensors 65*a*–65*c* connected to said treatment planning system 63 via suitable connections 65*a*'–65*c*' are positioned within the patient's body cavity 66*a* surrounding the X-ray radiation emitting anode 15 of the X-ray source device 67. These sensors measure the radiation dose as emitted by the anode 15 and generate measurement signals which are fed in the treatment planning system 63 via the connections 65*a*'–65*c*'. These radiation measurements serve as feedback information and these actual radiation measurements are compared with the preplanned treatment present in the treatment planning system 63. Based on this comparision the treatment planning system 63 controls MUX 60 via control means 62 until the actual dose distribution as measured by the radiation sensors 65*a*–65*c* matches the dose distribution as preplanned by the treatment planning system 63.

It will be clear that also more radiation sensors can be applied in order to obtain a more accurate comparison between the preplanned dose distribution and the actually administered dose distribution.

The invention claimed is:

1. A solid state brachytherapy applicator for performing radiation therapy treatment in an animal body, said applicator comprising:

an x-ray emitting surface;

a vacuum cavity having spatial geometry and containing a cathode and an anode spaced apart at a first distance from each other;

emitting means for emitting free electrons from the cathode;

electric field means for applying a high-voltage electric field between said cathode and said anode for accelerating said emitted free electrons towards said anode;

said vacuum cavity being at least partly transparent to X-ray radiation emitted by said anode;

said vacuum cavity being bound by first and second plate-shaped elements spaced at a second distance from each other, said first plate-shaped element serving as said cathode and said second plate-shaped element serving as said anode, said first and second plate shaped elements having longitudinal dimensions substantially greater than said first distance; and wherein during use said x-ray emitting surface is brought into contact with tissue of the animal body to be treated thereby emitting x-ray radiation having a dose contribution conformal to the spatial geometry of the vacuum cavity.

2. Solid state brachytherapy applicator according to claim 1, wherein spacers of high insulating material are present between said first and second plate-shaped elements.

3. Solid state brachytherapy applicator according to claim 1, wherein a getter material is provided on the surface of said first plate-shaped element facing away from said second plate-shaped element.

4. Solid state brachytherapy applicator according to claim 3, wherein said first plate-shaped element is provided with at least one opening exposing said getter material to said vacuum cavity.

5. Solid state brachytherapy applicator according to claim 1, wherein the solid state brachytherapy applicator is connected to a distal end of a guiding wire for insertion towards said desired location within an animal body.

6. Solid state brachytherapy applicator according to claim 1, wherein said first plate-shaped element serving as cathode is of a gated field emission type containing a ferro-electric electron emitting material.

7. Solid state brachytherapy applicator according to claim 6, wherein said ferro-electric electron emitting material is positioned between a lower electrode and an upper electrode, both electrodes being connected to a driving voltage.

8. Solid state brachytherapy applicator according to claim 7, wherein said lower electrode is built up from several electrode segments, the segments of said electrode being electrically isolated from each other and each separately being connected to said driving voltage.

9. Solid state brachytherapy applicator according to claim 8, wherein said electrode segments of said lower electrode are each separately connected to said driving voltage via a multiplexer.

10. Solid state brachytherapy applicator according to claim 7, wherein said upper electrode is constructed as an electrically conductive sheet provided with a large number of openings serving as emitting holes for the emitted free electrons.

11. Solid state brachytherapy applicator according to claim 10, wherein said openings have a polygonal shape.

12. Solid state brachytherapy applicator to claim 7, wherein said upper electrode is constructed as at least one electrically conductive frame in which a large number of disc shaped elements partly is fixed on the ferro-electric electron emitting material.

13. Radiation therapy treatment system for performing radiation therapy treatment in an animal body at least comprising:

a doses planning device for preplanning a radiation therapy treatment within said animal body using a solid state brachytherapy applicator;
said brachytherapy applicator including;
an x-ray emitting surface;
a vacuum cavity having spatial geometry and containing a cathode and anode spaced apart at a first distance from each other;
emitting means for emitting free electrons from the cathode;
electric field means for applying a high-voltage electric field between said cathode and said anode for accelerating said emitted free electrons towards said anode;
said vacuum cavity being at least partly transparent to X-ray radiation emitted by said anode;
said vacuum cavity being bound by first and second plate-shaped elements spaced at a second distance from each other, said first plate-shaped element serving as said cathode and said second plate-shape element serving as said anode, said first and second plate shaped elements having longitudinal dimensions substantially greater than said first distance; and
wherein during use said x-ray emitting surface is brought into contact with the tissue of animal body to be treated thereby emitting x-ray radiation having a dose contribution conformal to the spatial geometry of the vacuum cavity;
control means for driving said solid state brachytherapy applicator according to the preplanned therapy treatment; and
one or more radiation detectors positioned in the near vicinity of said source device in said animal body for measuring the actual radiation dose distribution generated by said solid state brachytherapy applicator, and wherein said radiation therapy treatment system is arranged for delivering feedback information to the control means to adapt the dose according to the preplanned treatment parameters.

14. Method for performing radiation therapy treatment in an animal body using a radiation therapy treatment system, said system comprising;
a doses planning device for preplanning a radiation therapy treatment within said animal body using a solid state brachytherapy applicator;
said brachytherapy applicator including;
an x-ray emitting surface;
a vacuum cavity having spatial geometry and containing a cathode and an anode spaced apart at a first distance from each other;
emitting means for emitting free electrons from the cathode;
electric field means for applying a high-voltage electric field between said cathode and said anode for accelerating said emitted free electrons towards said anode;
said vacuum cavity being at least partly transparent to X-ray radiation emitted by said mode;
said vacuum cavity being bound by first and second plate-shaped elements spaced at a second distance from each other, said first plate-shaped element serving as said cathode and said second plate-shape element serving as said anode, said first and second plate shaped elements having longitudinal dimensions substantially than said first distance; and
wherein during use said x-ray emitting surface is brought into contact with the tissue of animal body to be treated thereby emitting x-ray radiation having a dose contribution conformal to the spatial geometry of the vacuum cavity;
control means for driving said solid state brachytherapy applicator according to the preplanned therapy treatment; and
one or more radiation detectors positioned in the near vicinity of said source device in said animal body for measuring the actual radiation dose distribution generated by said solid state brachytherapy applicator, and wherein said radiation therapy treatment system is arranged for delivering feedback information to the control means to adapt the dose according to the preplanned treatment parameters.

15. Solid state brachytherapy applicator according to claim 1, wherein said first plate-shaped element serving as cathode is of a gated field emission type containing carbon nanotubes.

* * * * *